(12) United States Patent
Ibert et al.

(10) Patent No.: US 9,388,152 B2
(45) Date of Patent: Jul. 12, 2016

(54) METHOD FOR SYNTHESISING 2,5-FURANDICARBOXYLIC ACID FROM A COMPOSITION CONTAINING FURAN-2,5-DIALDEHYDE

(71) Applicant: ROQUETTE FRERES, Lestrem (FR)

(72) Inventors: Mathias Ibert, La Chapelle d'Armentieres (FR); Flora Chambon, Marc en Baroeul (FR); Laurent Dambrine, Sains en Gohelle (FR)

(73) Assignee: ROQUETTE FRERES, Lestrem (FR)

( * ) Notice: Subject to any disclaimer, the term of this patent is extended or adjusted under 35 U.S.C. 154(b) by 0 days.

(21) Appl. No.: 14/431,540

(22) PCT Filed: Sep. 26, 2013

(86) PCT No.: PCT/FR2013/052273
§ 371 (c)(1),
(2) Date: Mar. 26, 2015

(87) PCT Pub. No.: WO2014/049276
PCT Pub. Date: Apr. 3, 2014

(65) Prior Publication Data
US 2015/0274687 A1 Oct. 1, 2015

(30) Foreign Application Priority Data
Sep. 27, 2012 (FR) ...................................... 12 59103

(51) Int. Cl.
*C07D 307/68* (2006.01)
*C07D 307/46* (2006.01)

(52) U.S. Cl.
CPC ............ *C07D 307/68* (2013.01); *C07D 307/46* (2013.01)

(58) Field of Classification Search
CPC .................................................... C07D 307/68
USPC ......................................................... 549/485
See application file for complete search history.

(56) References Cited

U.S. PATENT DOCUMENTS

2007/0232815 A1 10/2007 Miura et al.
2014/0378691 A1 12/2014 Dambrine et al.

FOREIGN PATENT DOCUMENTS

| FR | 1 162 343 A | 11/1956 |
|---|---|---|
| FR | 2 669 634 A1 | 5/1992 |
| FR | 2 723 945 A1 | 3/1996 |
| WO | 2012/004069 A1 | 1/2012 |
| WO | 2012/017052 A1 | 2/2012 |
| WO | 2013/093322 A1 | 6/2013 |

OTHER PUBLICATIONS

Tony et al.: "Synthese de L'Hydroxymethyl-5 Furanne Carboxaldehyde-2 Et de Ses Derives Par Traitement Acide de Sucres sur Resines Echangeuses D'Ions", Bulletin de la Societe Chimique de France, Societe Francaise de Chimie. Paris, France, vol. 5, Jan. 1, 1987, pp. 855-860, XP009002108, ISSN: 0037-8968 p. 857; compounds 1,2,4.
Werpy, T., Peterson, G., "Top Value Added Chemicals from Biomass" vol. 1—Results of Screening for Potential Candidates from Sugars and Synthesis Gas, 2004. Top Value Added Chemicals from Biomass, vol. 1, pp. 26-28.
Andrisano, R.et al.: "Research into the migration of the carboxyl group in heterocyclical systems" Note I. On the preparation of 2-5-furandicarboxylic acid from furoic acid.Chim. (Rome) 1963, 53, 1658).
Koopman et al.: "Identification and characterization of the furfural and 5-(hydroxymethyl) furfural degradation pathways of Cupriavidus basilensis HMF14", PNAS Early Edition, pp. 1-6, Edited by Lonnie O'Neal Ingram, University of Florida, Gainesville, Gainesville, FL, and approved Jan. 19, 2010 (received for review Nov. 11, 2009).
Dae-Wi Yoon et al.: "Benzene-, Pyrrole-, and Furan-Containing Diametrically Strapped Calix[ 4]pyrroles-An Experimental and Theoretical Study of Hydrogen-Bonding Effects in Chloride Anion Recognition", © 2008 Wiley-VCH Verlag GmbH &. Co. KGaA, Weinheim, Angew. Chem. Int. Ed. 2008, 47, 5038-5042.
International Search Report, dated Jan. 21, 2014, from corresponding PCT application.
Hajj et al., "Synthesis of 5-hydroxymethyl-2-furancarboxaldehyde and derivatives thereof by acid treatment of sugars on ion exchange resins," Bulletin de la Societe Chimique de France, Societe Francaise de Chimie. Paris, France, vol. 5, Jan. 1, 1987, pp. 855-860, XP009002108, ISSN: 0037-8968 p. 857; compounds 1,2,4.

*Primary Examiner* — Taofiq A Solola
(74) *Attorney, Agent, or Firm* — Young & Thompson

(57) ABSTRACT

A method for synthesizing 2,5-furandicarboxylic acid (FDCA) from furan-2,5-dialdehyde (DFF). The method is industrially applicable due to the simplicity and availability of the reagents used, and due to the experimental conditions on which the method is based: the method requires low temperatures and enables a reaction under atmospheric pressure, the reaction times being relatively short. Furthermore, the method does not lead to the formation of salts that need to be treated downstream from the method, and the catalytic ratio relative to the initial product is particularly low.

17 Claims, No Drawings

METHOD FOR SYNTHESISING 2,5-FURANDICARBOXYLIC ACID FROM A COMPOSITION CONTAINING FURAN-2,5-DIALDEHYDE

The present invention relates to a process for synthesizing 2,5-furandicarboxylic acid (FDCA), from a composition containing furan-2,5-dialdehyde (DFF). Such a process is readily industrializable: it is very simple to carry out, the reagents used are readily available, and the experimental conditions on which it is based are very "mild", namely low temperatures and atmospheric pressure. Furthermore, it does not lead to the formation of salts that need to be treated downstream. Finally, the amount of catalyst involved relative to the initial product is particularly low, thereby representing an undeniable economic advantage considering the price of said catalyst.

The present invention thus relates to a process for producing 2,5-furandicarboxylic acid, denoted under the term FDCA and corresponding to the following chemical formula:

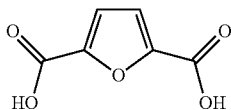

FDCA is used in pharmacology, where its diethyl ester has shown a strong anesthetic activity, comparable to that of cocaine. It is also a very powerful chelating agent which makes it possible to complex numerous ions such as $Ca^{2+}$, $Cu^{2+}$ and $Pb^{2+}$. In medicine, it is used for treating kidney stones, but also in the preparation of transplants having biological properties similar to those of natural organs, and which are characterized by an absence of rejection after transplantation.

However, FDCA is first and foremost a base monomer which is part of the production of numerous polymers, such as polyesters, polyamides or else polyurethanes, making it possible in particular to improve the mechanical properties thereof. In polyesters, it is capable of being used to replace phthalates. From the viewpoint of such a possibility, FDCA has been classified among the 12 vegetable-derived raw materials which offer the greatest industrial potential (Werpy, T., Peterson, G., 2004. Top Value Added Chemicals from Biomass, vol. 1, pp. 26-28).

At the current time, there are 4 routes for the synthesis of FDCA. The first is based on the dehydration of hexose derivatives. Such a reaction is possible only under very severe operating conditions: the use of highly concentrated acid solutions, a temperature greater than 120° C. and reaction times of about half a day. Document FR 2 723 945 is an illustration thereof.

Another route consists in performing the catalytic conversion of furan derivatives. Furfural can, for example, be oxidized by means of nitric acid to give 2-furoic acid, the latter then being converted into its methyl ester. The ester is converted by chloromethylation into 5-chloromethylfuroate. The latter is oxidized once again using nitric acid so as to form 2,5-dimethyl furandicarboxylate which, after alkaline hydrolysis, produces FDCA with a yield of only about 50%. In parallel, it has been demonstrated that potassium 2-furoate, heated at 300° C. under a nitrogen atmosphere, produces dipotassium 2,5-furandicarboxylate (Andrisano, R.; Angeloni, A. S. Ann. Chim. (Rome) 1963, 53, 1658).

A third possibility, which is without doubt at the current time the most widely used industrially, consists in oxidizing furan derivatives disubstituted in position 2 and 5, including 5-hydroxymethyl furaldehyde (5-HMF) and furan-2,5-dialdehyde or 2,5-diformylfuran (DFF). Thus, patent FR 2 669 634 describes a process for the catalytic oxidation of 5-HMF resulting in the synthesis of FDCA. This process consists in oxidizing 5-HMF in an alkaline aqueous medium, under an oxygen stream, in the presence of a carbon-supported, lead-activated, platinum-based catalyst. Such a process has the drawback of generating large amounts of salts.

Similarly, patent WO 2012/017052 describes the synthesis of FDCA by oxidation of 5-HMF in a basic medium in the presence of a carbon-supported platinum catalyst, at 100° C. and under a pressure of 5 bar, with the formation of a large amount of salts.

DFF can also be used as a starting product, as disclosed in patent US 2007/0232815. Described therein is the synthesis of FDCA by oxidation of DFF in an alkaline aqueous medium, in the presence of oxygen, the catalyst being in particular potassium permanganate. Nevertheless, this process, which results in an 89% yield, makes reference to a very high catalytic ratio with respect to the DFF, equal to 195% (weight ratio) in the example 4 thereof.

Along these lines, the document "Synthèse de l'hydroxyméthyl-5 furanne carboxaldehyde-2 et de ses dérivés par traitement acide de sucres sur résines échangeuses d'ions" [synthesis of 5-hydroxymethylfuran-2-carboxaldehyde and of derivatives thereof by acid treatment of sugars on ion exchange resins] (Bulletin de la Société Chimique de France [Bulletin of the French Chemical Society], Soc. Fr. de Chim., vol 5, Jan. 1, 1987, pp. 855-860) discloses, on page 859, the reaction of DFF to FDCA, catalyzed by silver oxide in an aqueous sodium hydroxide solution. The reaction yield is 80%, with a catalyst-to-DFF weight ratio equal to 222.5%.

Finally, still in this category, the document "Benzene-, Pyrrole-, and Furan-containing diametrically strapped calix [4]pyrroles—An experimental and theoretical study of hydrogen-bonding effects in chloride anion recognition" (Angewandte Chemie International Edition, vol 47, no. 27, Jun. 23, 2008, pp. 5038-5042) describes the synthesis of FDCA from DFF (scheme 1) in the presence of $KMnO_4$ in an aqueous sodium hydroxide solution. The yield is 60%, but no catalytic ratio (catalyst/DFF weight ratio) is mentioned.

It is important to note that these three documents in fact result in the synthesis of FDCA salts, and not of FDCA as such, since the syntheses are all carried out in a basic medium (presence of an aqueous sodium hydroxide solution).

Finally, there is a fourth type of process, which is based on the enzymatic conversion of 5-HMF into FDCA in the presence of molecular oxygen, and using a 5-HMF/furfural oxydoreductase, which has been isolated from the bacterium Cupriavidus basilensis HMF14 (F. Koopman, N. Wierckx, J. H. de Winde and H. J. Ruijssenaars. Proc. Nat. Acad. Sci. USA. 2010, 107: 4919-4924). This process makes it possible to work at ambient pressure and temperature, in water, and offers a yield of about 97% for a final composition having an FDCA content greater than 99%. Nevertheless, the enzyme used is at the current time produced on an extremely small scale, which is not compatible with the requirements of an industrial process. Furthermore, this process generates a not insignificant amount of salts.

In summary, the processes for synthesizing FDCA according to the prior art have the drawbacks of operating under excessively severe temperature and/or pressure conditions, of generating large amounts of salts that must subsequently be treated, of offering mediocre yields, of using a high catalytic ratio, i.e. of consuming too much catalyst, and of producing only very mediocre yields, or of relying on a very particular enzyme, the supply of which is not at the current time assured with a view to industrial production.

Pursuing research in order to overcome such drawbacks, the applicant has succeeded in developing a novel process for producing FDCA, based on the oxidation of DFF, under particularly mild temperature and pressure conditions (temperature less than 100° C., and atmospheric pressure). In addition, this process can be carried out in water, with very advantageous catalytic ratios (less than 1 mol of catalyst per mol of DFF). Furthermore, there is no formation of salts, thereby avoiding any problem of subsequent retreatment or treatment.

The production of FDCA with a degree of conversion of 100% and a final product content greater than 70% by weight, preferentially than 80%, very preferentially than 90%, and extremely preferentially greater than 99%, along with an FDCA selectivity greater than 70%, preferentially than 80%, very preferentially than 90%, is thus achieved. Yields which are for the most part greater than 80% by weight of FDCA thus formed are therefore achieved.

In addition, it is not necessary to start from a composition which has a high DFF content in order to obtain a high FDCA selectivity (>75%). Indeed, according to one particular variant, a mixture of DFF/FFCA (5-furaldehyde-2-carboxylic acid) resulting from the oxidation of 5-HMF (according to the technology as patented by the applicant in the document bearing the filing number FR 11 62343) can be used as starting reagent.

As already explained, the process which is the subject of the present invention makes it possible to directly obtain FDCA and not a salt thereof. This process is in particular characterized in that it is carried out in an acidic medium (pH<7).

Throughout the present application, the terms selectivity (S), conversion (C) and yield (Y) are used with reference to the following definitions:

$C$ (mol %)=((amount of DFF converted)×100)/initial amount of DFF $S$ (mol %)=((amount of FDCA formed)×100)/amount of DFF converted $Y$ (mol %)=$S \times C$/100=((amount of FDCA formed× 100)/initial amount of DFF)

Thus, a first subject of the present invention consists of a process for synthesizing FDCA at a pH of less than 7, by bringing the following into contact:
 a) a composition containing DFF,
 b) a protic solvent,
 c) a source of oxidizing agent,
 d) and an oxidation catalyst,
and characterized in that the ratio between catalyst and DFF is between 0.01% and 5% by weight (relative to the DFF), more preferably between 0.1% and 3% by weight.

Entirely surprisingly, the present invention makes it possible not only to obtain FDCA directly, with very high degrees of conversion and very high yields, but also to do so while extremely substantially reducing the amounts of catalyst used. When the cost of these catalysts, which are generally products resulting from complex syntheses, and their dangerousness with respect to human beings but also to the environment, are considered from the viewpoint of this result, all the advantage of the process which is the subject of the present invention can be understood.

The starting reagent is thus a composition containing DFF. In this respect, it may be DFF alone or as a mixture with at least one other constituent. Advantageously, when the DFF is not present alone in the composition, said composition will consist of a composition or mixture of DFF/FFCA in any proportions. Particularly advantageously, this mixture results from the oxidation of 5-HMF according to the process which is the subject of the invention patented by the applicant under number FR 11 62343.

The process which is the subject of patent FR 11 62343 mentioned above is characterized in that it comprises a step of oxidation in the presence of at least one organic acid, of a nitroxyl radical, of an oxygen source and of an oxygen transfer agent. The nitroxyl radical is in particular chosen from (2,2,6,6-tetramethylpiperidine-1-yl)oxyls, also called TEMPO. In agreement with this variant, the process according to the invention therefore has the advantage of synthesizing FDCA in a "one-pot" process, starting from 5-HMF: by oxidation of 5-HMF to give a DFF/FFCA mixture according to the method described in patent FR 11 62343 without the purification step, then oxidation of this mixture to give FDCA according to the present invention.

The process which is the subject of the present invention is thus characterized in that the synthesis of FDCA resulting from bringing the above mentioned compounds into contact is carried out at a pH of less than 7, preferentially less than 4, very preferentially less than 1. The pH is adjusted by any of the means well known to those skilled in the art, in particular by adding an acid to the medium to be acidified.

The protic solvent used in the present invention at the level of the FDCA synthesis is chosen from water, alcohols, such as monoalcohols, and organic acids, or mixtures thereof, preferentially from water and acetic acid, and mixtures thereof. The formation of salts which require means for subsequent treatment, as in the techniques for oxidation of furan derivatives disubstituted in position 2 and 5, is thus prevented.

The source of oxidizing agent is in particular chosen from aqueous hydrogen peroxide solution, peracetic acid and the product sold under the brand BACTIPAL® (or homologues under other tradenames), which is a mixture of peracetic acid and hydrogen peroxide, and also from mixtures of these constituents, peracetic acid being the most preferred. The applicant has noted that, when peracetic acid is used, it should be introduced dropwise rather than right at the beginning of the reaction, so as to improve the FDCA selectivity.

The oxidation catalyst is in particular chosen from the homogeneous oxidation catalysts well known to those skilled in the art, and in particular from the conventional metallic oxidation catalysts (based on Ru, Mn, Cr, Mo, Zn, Fe, Cu, V) in chloride, bromide, sulfate, nitrate, oxide or acid form, said catalyst being more preferentially either $KMnO_4$ or $RuCl_3$. In addition, it is not necessary to use a co-catalyst.

The oxidation reaction is carried out at a temperature between 3° C. and the reflux temperature of the solvent (heating to boiling of the solvent), preferentially between 10° C. and the reflux temperature of the solvent (heating to boiling of the solvent), and even more preferentially at a temperature between 40° C. and 60° C. It can optionally take place under pressure, but it is advantageously carried out at atmospheric pressure. Such conditions are particularly "mild" and easy to implement, in particular compared with those described in the prior art concerning the catalytic conversion of furan derivatives.

The contact time between the various constituents a), b), c) and d) is between 1 minute and 8 hours, preferentially between 15 minutes and 2 hours. These are relatively short reaction times, in particular compared with those envisioned in document F 2 723 945.

The number of molar equivalents of oxidizing agent relative to DFF is between 0.1 and 10, more preferentially between 2.5 and 5.

As for the rest, the oxidation process of the present invention can be carried out in batch or fixed-bed reactors of any type, under pressure or not under pressure, preferentially not under pressure. The type of batch reactor may be a flat-bottomed round pyrex flask, equipped with a magnetic stirrer bar. Preferentially, the reactor also has a system for the dropwise introduction of the source of oxidizing agent. The reactor may in addition comprise a cooling system and also a system for measuring and regulating the temperature.

During the oxidation process, the reaction medium is kept stirring. The stirring speed is preferentially adjusted between 100 and 500 revolutions/minute, more preferentially between 100 and 250 revolutions/minute.

Another advantage relating to the process according to the present invention lies in the recovery of the FDCA, which is particularly easy, since the FDCA in question is precipitated during its formation; it can therefore be recovered, in particular using physical means, either at the end of the reaction, or advantageously during the reaction, i.e. it is continually drawn off during said reaction. This easy recovery therefore allows recycling of the excess catalyst and oxidizing agent and also of the solvent.

The examples which follow make it possible to understand the present invention more clearly, without, however, limiting the scope thereof.

EXAMPLES

The following tables 1 to 3 list the experimental conditions of various syntheses which were carried out according to the same protocols as those described hereinafter:

In this experiment, which corresponds to test no. 3, the following are used:
 a composition containing DFF (95.1% by weight of DFF and 4.9% by weight of FFCA): 4 g
 $KMnO_4$ (solution at 0.02 mol/l): 2.53 g
 demineralized water: 36 ml
 peracetic acid (solution at 38%): 36 g
Operating Conditions:
 Reaction temperature: 50° C.
 Reaction time: 2 h00 (peracetic acid introduction)+3 h00 (contact time)

4 g of a composition containing DFF and 2.53 g of a solution of $KMnO_4$ at 0.02 mol/l, then 36 g of demineralized water are placed in a flat-bottomed single-necked round flask. The ratios are established so as to have 0.2% by weight of $KMnO_4$ relative to the weight of DFF, and also a molar equivalent of oxidizing agent relative to DFF of 5.

The round flask is placed with magnetic stirring in a water bath so as to reach a reaction temperature of 50° C. 36 g of a solution of peracetic acid at 38% by volume are added, with magnetic stirring, dropwise at a rate of 0.3 g/min (i.e. approximately 2 h00 of dropwise introduction), leading to a gradual acidification of the reaction medium. At the end of the addition of peracetic acid, the reaction medium is left to stir for a further 3 h00. The reaction medium then has a pH of less than 0.5. The magnetic stirring is then stopped and the reaction medium is analyzed by gas chromatography.

The degree of conversion and also the selectivity of the reaction with regard to FDCA is then determined.
Description Test No. 17

In this experiment, which corresponds to test no. 17, the following are used:
 a composition containing DFF (93.4% by weight of DFF): 1.2 g
 perchloric acid $HClO_4$: 1.15 g
 methanol: 46 g
 $FeCl_3$: 0.11 g, i.e. 9% by weight/composition containing DFF
 hydrogen peroxide (30% solution): 8.6 g
Operating Conditions:
 Reaction temperature: 5° C.
 Reaction time: 10 minutes (hydrogen peroxide introduction)+4 h00 (contact time)

1.2 g of a composition containing DFF, 1.15 g of perchloric acid, 0.11 g of $FeCl_3$ and then 46 g of methanol are placed in a flat-bottomed single-necked round flask. The ratios are established so as to have 9% by weight of $FeCl_3$ relative to DFF, and also a molar equivalent of oxidizing agent relative to DFF 7.8.

The round flask is placed under magnetic stirring, then the reaction mixture is brought to a reaction temperature of 5° C. 8.6 g of a solution of hydrogen peroxide at 30% by volume are added, with magnetic stirring, dropwise over the course of a total time of 10 minutes. At the end of the addition of hydrogen peroxide, the reaction medium is left to stir for 4 h00. The reaction temperature is then brought back to ambient temperature, and then the magnetic stirring is stopped. The reaction medium is then analyzed by gas chromatography.

The degree of conversion and also the selectivity of the reaction with regards to FDCA are then determined.

It should be noted that all of the tests are carried out at a pH of between 0 and 3, and lead to the production of FDCA directly, and not to a salt thereof.

TABLE 1

| Test no. | Mass composition containing DFF (g) | Solvent (mass g) |
|---|---|---|
| 1 | 4 | water (36) |
| 2 | 4 | water (36) |
| 3 | 4 | water (36) |
| 4 | 2 | acetic acid (18) |
| 5 | 2 | acetic acid/water (12/6) |
| 6 | 2 | water (18) |
| 7 | 2 | water (18) |
| 8 | 2 | acetic acid (18) |
| 9 | 2 | water (18) |
| 10 | 2 | water (18) |
| 11 | 2 | water (18) |
| 12 | 2 | water (18) |
| 13 | 2 | water (18) |
| 14 | 2 | water (18) |
| 15 | 2 | water (18) |
| 16 | 2 | water (18) |
| 17 | 1.2 | MeOH/$HClO_4$ (46/1.15) |
| 18 | 1.2 | MeOH/$HClO_4$ (46/1.15) |

TABLE 2

| | Source of oxidizing agent | | | |
|---|---|---|---|---|
| Test no. | Oxidizing agent | Mass (g) | Number of molar equivalents of oxidizing agent relative to DFF | Oxidizing agent introduction time |
| 1 | peracetic acid (38%) | 32.1 | 5 | 3h00 |
| 2 | peracetic acid (38%) | 16.1 | 2.5 | 1h30 |
| 3 | peracetic acid (38%) | 36 | 5.6 | 3h00 |

TABLE 2-continued

| Test no. | Source of oxidizing agent | | | |
|---|---|---|---|---|
| | Oxidizing agent | Mass (g) | Number of molar equivalents of oxidizing agent relative to DFF | Oxidizing agent introduction time |
| 4 | peracetic acid (38%) | 16 | 5 | 2h00 |
| 5 | peracetic acid (38%) | 16 | 5 | 2h00 |
| 6 | BACTIPAL ® | 16 | 5$_{min}$ 10$_{max}$ (manufacturer data range) | 2h00 |
| 7 | BACTIPAL ® | 16 | 5$_{min}$ 10$_{max}$ (manufacturer data range) | 2h00 |
| 8 | peracetic acid (38%) | 16 | 5 | 2h00 |
| 9 | peracetic acid (38%) | 16 | 5 | 0h30 |
| 10 | peracetic acid (38%) | 8 | 2.5 | 1h10 |
| 11 | peracetic acid (38%) | 16 | 5 | 2h00 |
| 12 | peracetic acid (38%) | 16 | 5 | 2h00 |
| 13 | peracetic acid 38% | 16 | 5 | 2h00 |
| 14 | peracetic acid (38%) | 16 | 5 | 2h00 |
| 15 | peracetic acid (38%) | 16 | 5 | 2h00 |
| 16 | peracetic acid (38%) | 16 | 5 | 2h00 |
| 17 | $H_2O_2$ 30% | 8.6 | 7.8 | 10 minutes |
| 18 | $H_2O_2$ (30%) | 8.6 | 7.8 | 10 minutes |

TABLE 3

| Test no. | Oxidation catalyst | | |
|---|---|---|---|
| | Catalyst | Mass (g) | % or ratio by weight catalyst/composition containing DFF |
| 1 | $RuCl_3$ | 0.068 | 1.7 |
| 2 | $RuCl_3$ | 0.068 | 1.7 |
| 3 | $KMnO_4$ (0.02 mol/l) | 2.53 | 0.2 |
| 4 | $KMnO_4$ (0.02 mol/l) | 4.03 | 0.63 |
| 5 | $KMnO_4$ (0.02 mol/l) | 1.26 | 0.2 |
| 6 | $KMnO_4$ (0.02 mol/l) | 4.03 | 0.63 |
| 7 | $KMnO_4$ (0.02 mol/l) | 4.03 | 0.63 |
| 8 | $KMnO_4$ (0.02 mol/l) | 4.03 | 0.63 |
| 9 | $KMnO_4$ (0.02 mol/l) | 1.2 | 0.2 |
| 10 | $KMnO_4$ (0.02 mol/l) | 0.4 | 0.063 |
| 11 | $KMnO_4$ (0.02 mol/l) | 0.4 | 0.063 |
| 12 | $K_2Cr_2O_7$ | 0.06 | 3 |
| 13 | $MoH_2O_4$ | 0.04 | 2 |
| 14 | $ZnCl_2$ | 0.035 | 1.75 |
| 15 | $FeCl_2$ | 0.035 | 1.75 |
| 16 | $FeCl_3$ | 0.045 | 2.25 |
| 17 | $FeCl_3$ | 0.11 | 9 |
| 18 | $Fe_2(SO_4)_3 \cdot 5H_2O$ | 0.24 | 20 |

Table 4 indicates the reaction times and the temperature, and also the DFF contents, the selectivity and the conversion, relating to the oxidation reactions.

TABLE 4

| Test no. | Reaction temperature (° C.) | Total time | Composition containing DFF | | FDCA | |
|---|---|---|---|---|---|---|
| | | | DFF content (% by weight) | FFCA content (% by weight) | Conversion (%) | selectivity (%) |
| 1 | 50 | 6h00 | 99.3 | 0.7 | 100 | 91.7 |
| 2 | 60 | 3h30 | 99.3 | 0.7 | 100 | 75 |
| 3 | 50 | 5h00 | 95.1 | 4.9 | 100 | 91 |
| 4 | 50 | 5h00 | 73.3 | 26.7 | 100 | 87.2 |
| 5 | 50 | 5h00 | 73.3 | 26.7 | 100 | 84.7 |
| 6 | 50 | 5h00 | 73.3 | 26.7 | 100 | 80.5 |
| 7 | 30 | 5h00 | 73.3 | 26.7 | 100 | 66.2 |
| 8 | 40 | 5h00 | 73.3 | 26.7 | 100 | 77.5 |
| 9 | 50 | 0h45 | 93.1 | 6.9 | 100 | 72.6 |
| 10 | 50 | 1h10 | 93.1 | 6.9 | 100 | 70.7 |
| 11 | 50 | 2h15 | 93.1 | 6.9 | 100 | 80.5 |
| 12 | 50 | 5h00 | 73.3 | 26.7 | 100 | 87.2 |
| 13 | 50 | 5h00 | 73.3 | 26.7 | 100 | 80.1 |
| 14 | 50 | 5h00 | 73.3 | 26.7 | 100 | 77 |
| 15 | 50 | 5h00 | 73.3 | 26.7 | 100 | 45 |
| 16 | 50 | 5h00 | 73.3 | 26.7 | 100 | 49.1 |
| 17 | 5 | 4h00 | 93.4 | 6.6 | 94 | 72* |
| 18 | 5 | 4h00 | 91.7 | 8.3 | 92 | 73* |

*for the results of tests 17 and 18, the selectivity corresponds to the sum of the carboxylic function and methyl ester function selectivities.

The examples, and in particular the values obtained according to table 4, demonstrate that the process according to the present invention makes it possible to obtain FDCA with a degree of conversion of 100%. The FDCA selectivity is always greater than 70%, and sometimes even than 90%.

A process has thus been successfully developed which is easily industrializable by virtue of its simplicity and the availability of the reagents used, and by virtue of the experimental conditions that it requires: working at atmospheric pressure and at low temperatures (of about 50° C. in the examples), the reaction times being relatively short (sometimes less than 1 hour). Furthermore, no salts which need to be treated downstream of the process are formed, and the catalytic ratio relative to the initial product, a weight ratio, is particularly low. By reducing the amount of catalyst involved, the overall cost of the process is reduced accordingly, and the risks associated with the dangerousness of the catalyst with respect to humans and the environment are limited.

The invention claimed is:

1. A process for synthesizing 2,5-furandicarboxylic acid (FDCA) at a pH of less than 7, comprising carrying out an oxidative reaction by bringing the following into contact:
   a) a composition containing furan-2,5-dialdehyde (DFF),
   b) a protic solvent,
   c) a source of oxidizing agent selected from the group consisting of aqueous hydrogen peroxide solution, peracetic acid and mixtures thereof, and
   d) a metallic oxidation catalyst based on a metal selected from the group consisting of Ru, Mn, Cr, Mo, Zn, Fe, Cu, and V, said metallic oxidation catalyst being in a form selected from the group consisting of chloride, bromide, sulfate, nitrate, oxide and acid,
wherein the weight ratio between catalyst and DFF is between 0.01% and 25%, and the reaction is carried out under pressure or at atmospheric pressure.

2. The process as claimed in claim 1, wherein the composition a) containing DFF is a mixture of DFF and 5-furaldehyde-2-carboxylic acid (FFCA) in any proportions.

3. The process as claimed in claim 1, wherein the composition containing DFF results from the oxidation of 5-hydroxymethyl furaldehyde (5-HMF) in the presence of at least one organic acid, of a nitroxyl radical, of an oxygen source and of an oxygen transfer agent.

4. The process as claimed in claim 1, wherein the protic solvent b) is selected from the group consisting of water, alcohols, organic acids, and mixtures thereof.

5. The process as claimed claim 1, wherein the oxidation reaction is carried out at a temperature between 3° C. and the reflux temperature of the solvent.

6. The process as claimed in claim 1, wherein the pressure corresponds to atmospheric pressure.

7. The process as claimed in claim 1, wherein the contact time between the various constituents a), b), c) and d) is between 1 minute and 8 hours.

8. The process as claimed in claim 1, wherein the number of molar equivalents of oxidizing agent relative to DFF is between 0.1 and 10.

9. The process as claimed in claim 1, wherein the weight ratio between catalyst and DFF is between 0.01% and 10% by weight.

10. The process as claimed in claim 9, wherein the weight ratio between catalyst and DFF is between 0.1% and 3% by weight.

11. The process as claimed in claim 1, wherein the oxidizing agent c) is peracetic acid and is introduced dropwise.

12. The process as claimed in claim 1, wherein the metallic oxidation catalyst d) is either $KMnO_4$ or $RuCl_3$.

13. The process as claimed in claim 4, wherein the protic solvent b) is selected from the group consisting of water, acetic acid and mixtures thereof.

14. The process as claimed in claim 4, wherein the protic solvent b) comprises methanol.

15. The process as claimed in claim 5, wherein the oxidation reaction is carried out at a temperature between 40° C. and 60° C.

16. The process as claimed in claim 7, wherein the contact time is between 15 minutes and 2 hours.

17. The process as claimed in claim 8, wherein the number of molar equivalents of oxidizing agent relative to DFF is between 2.5 and 5.

* * * * *